United States Patent [19]

Lohaus et al.

[11] Patent Number: 5,286,867
[45] Date of Patent: Feb. 15, 1994

[54] SUBSTITUTED 1-SULFONYLOXY-2-PYRIDONES AND PROCESS FOR PREPARING THEM

[75] Inventors: Gerhard Lohaus, Kelkheim; Walter Spiess, Dieburg; Georg Pawlowski, Wiesbaden, all of Fed. Rep. of Germany

[73] Assignee: Hoechst Aktiengesellschaft, Frankfurt am Main, Fed. Rep. of Germany

[21] Appl. No.: 870,920

[22] Filed: Apr. 20, 1992

[30] Foreign Application Priority Data

Apr. 20, 1991 [DE] Fed. Rep. of Germany ....... 4112967

[51] Int. Cl.$^5$ .......................................... C07D 213/89
[52] U.S. Cl. .................... 546/249; 546/261; 546/269; 546/283; 546/284; 546/288; 546/294; 546/295
[58] Field of Search .............. 546/249, 261, 269, 283, 546/284, 288, 294, 295

[56] References Cited

U.S. PATENT DOCUMENTS

| | | | |
|---|---|---|---|
| 3,732,273 | 5/1973 | Heine et al. | 260/456 R |
| 4,197,080 | 4/1980 | Mee | 430/211 |
| 4,425,424 | 1/1984 | Altland et al. | 430/270 |
| 4,619,998 | 10/1986 | Buhr | 544/193.1 |
| 4,696,888 | 9/1987 | Buhr | 430/270 |

FOREIGN PATENT DOCUMENTS 0330386  8/1989  European Pat. Off. .

OTHER PUBLICATIONS

Taylor et al., "Thallium in Organic Synthesis", J. Org. Chem., 35, 1672, 1970, p. 1568.
Ueno et al., "Chemical Amplification Positive Resist Systems Using Novel Sulfonates as Acid Generators", in Polymers for Microelectronics-Science and Tech., edited by Y. Tabata et al., Kodansha-Weinheim-New York, 1989, pp. 66-67.

*Primary Examiner*—Richard L. Raymond
*Attorney, Agent, or Firm*—Foley & Lardner

[57] ABSTRACT

1-Sulfonyloxy-2-pyridones of the formula I

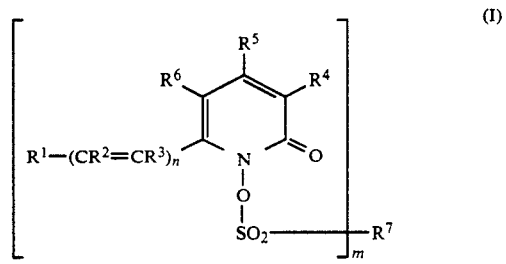

show good radiation sensitivity over a wide spectral range and are therefore valuable as photoactive compounds in radiation-sensitive mixtures.

19 Claims, No Drawings

SUBSTITUTED 1-SULFONYLOXY-2-PYRIDONES AND PROCESS FOR PREPARING THEM

BACKGROUND OF THE INVENTION

1. Field of the Invention

The invention relates to novel radiation-sensitive 1-sulfonyloxy-2-pyridones, chromophorically substituted in the 6-position, to a process for preparing them and to their use, preferably in a radiation-sensitive mixture.

2. Description of Related Art

The use of 1-sulfonyloxy-2-pyridones as photooxidants in radiation-sensitive mixtures which contain a leuco dye has been disclosed by U.S. Pat. No. 4,425,424. In such mixtures, the photooxidant effects during irradiation, for example, an oxidation, causes the leuco dye to undergo an intensive color change and causes a visual contrast between exposed and unexposed areas. Such color changes are desired in industry, for example in the production of printing forms, in order to enable the copying result to be assessed after exposure, and before development.

1-Benzenesulfonyloxy- and 1-(toluene-4-sulfonyloxy)-2-pyridone and processes for the preparation thereof are known (E. C. Taylor et al., J. Org. Chem., 35, 1672, 1970). The radiation sensitivity of these compounds was, however, not recognized.

Sulfonic acid esters as acid generators in radiationsensitive mixtures are known. Examples of these are the sulfonates of hydroxymethylbenzoin derivatives (see DE-A 1,919,678) or 2-nitrobenzyl sulfonates (see EP-A 0,330,386) and pyrogallol sulfonates (see T. Ueno et al., Chemical Amplification Positive Resist Systems Using Novel Sulfonates as Acid Generators, in "Polymers for Microelectronics - Science and Technology", edited by Y. Tabata et al., Kodansha-Weinheim-New York, 1989, pages 66–67). Such radiation-sensitive sulfonic acid esters are, due to their absorption properties, particularly suitable for irradiation with high-energy UV2 radiation, that is, 220 to 280 nm. However, their sensitivity to the UV3 and UV4 radiation (350 to 450 nm) currently used in industry is inadequate for use in practice.

Compounds which have sensitivities suitable for practice in this region are known from EP-A 0,137,452. These are, for example, compounds which contain trichloromethyl groups and, on exposure, from free chlorine radicals and hydrochloric acids, which confer the desired properties as photoinitiators or photo-acid generators on these compounds. The photolytically generated hydrohalic acids, however, have a strongly corrosive action and, for this reason, cannot be used in many technical fields.

SUMMARY OF THE INVENTION

It was therefore an object of the invention to provide radiation-sensitive compounds which, in particular, have high sensitivities in the region of radiation of a wavelength between 350 and 450 nm or in the visible region and can be prepared in a simple manner. At the same time, it was desired that the compounds according to the invention would also be sensitive to high-energy UV radiation, for example that emitted by KrF-excimer lasers. In accordance with the object of the invention, these compounds should, on irradiation, for active photo-products without a corrosive action, so that photoinitiators and photo-acid generators are provided which can also be used in conjunction with readily corrodible materials.

It was also an object of the present invention to provide a method for preparing these compounds.

It was further an object of the present invention to provide a method of using these compounds in radiation-sensitive mixtures.

In accomplishing the foregoing objectives, there has been provided in accordance with one aspect of the present invention, radiation-sensitive, chromophorically substituted 1-sulfonyloxy-2-pyridones of the formula I,

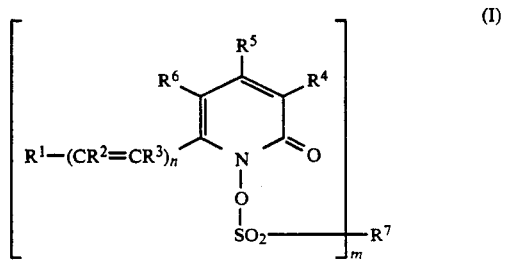

in which

R$^1$ is an alkyl, cycloalkyl, aryl, aralkenyl, heteroaryl or heteroaralkenyl radical, R$^2$ is hydrogen, chlorine, bromine or an alkyl, cycloalkyl, aryl or heteroaryl radical, or R$^1$ and R$^2$ together form a five- to eight-membered ring, R$^3$ is hydrogen or an alkyl radical, R$^4$ is hydrogen, halogen, nitro, acylamino, cyano, thiocyanato or an alkyl, alkenyl, alkynyl, aryl, aralkyl, alkylthio, arylthio or cycloalkylthio radical, R$^5$ is hydrogen or an alkyl or aryl radical or R$^4$ and R$^5$ together form a five- to eight-membered ring, R$^6$ is hydrogen, halogen, nitro, acylamino, cyano, thiocyanato or an alkyl, alkenyl, alkoxyalkyl, aryl, aralkyl, alkylthio, cycloalkylthio or arylthio radical, R$^7$ is an alkyl or cycloalkyl radical, a perfluorinated or highly fluorinated alkyl radical or an aryl, arylalkyl or heteroaryl radical or an alkylene or arylene radical, m is 1 or 2 and n is 1, 2 or 3.

When n or m or both m and n are greater than 1, the radicals R in the repeating units may be the same or different.

An alkyl radical is designated as "highly fluorinated", when 50% or more of alkyl hydrogen atoms are replaced by fluorine atoms.

In accordance with another object of the present invention, there has been provided a process for preparing a 1-sulfonyloxy-2-pyridone as described above, which comprises the steps of a) converting a 6-halogenomethyl-2-pyrone into a phosphonium compound or phosphono compound, b) subjecting this compound to a Wittig reaction or a variant thereof, c) converting the compound obtained into a 1-hydroxy-2-pyridone and d) reacting with a sulfonic acid halide to give a 1-sulfonyloxy-2-pyridone of the formula I.

A common variant of the Wittig reaction is, for example, the Horner-Emmons reaction in which phosphonates are employed instead of phosphorus -ylides.

In accordance with another object of the present invention there has been provided a method of using the inventive compounds in radiation sensitive mixtures, and radiation-sensitive recording materials.

Further objects, features and advantages of the present invention will become apparent form the detailed description of preferred embodiments that follows.

DETAILED DESCRIPTION OF PREFERRED EMBODIMENTS

The present invention is directed to all compounds falling within the scope of formula I. Those compounds of the formula I are preferred in which $R^1$ is an alkyl or cycloalkyl radical or an aryl radical of the formula II

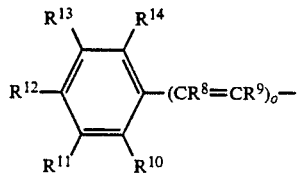

in which
  $R^8$ and $R^9$ are identical or different and are hydrogen or an alkyl (preferably having 1-6 carbon atom) or aryl group,
  $R^{10}$ to $R^{14}$ are identical or different and are hydrogen, an alkyl, alkenyl, alkoxy, alkylthio or alkanesulfonyl radical each having up to 6 carbon atoms, a cycloalkyloxy, cycloalkylthio or cycloalkanesulfonyl radical having up to 8 carbon atoms, a phenyl, styryl, phenoxy, phenylthio, benzenesulfonyl, phenylalkoxy, phenylalkylthio or phenylalkanesulfonyl radical which may be substituted on the aromatic ring and has up to 3 carbon atoms in the alkyl chain, hydroxy, halogen, trifluoromethyl, nitro, cyano, alkoxycarbonyl, carbamoyl which may be substituted on the nitrogen by one or two alkyl radical(s) which may be linked to form a 5- to 7-membered ring, sulfamoyl which may be substituted on the nitrogen by one or two alkyl radical(s) which may be linked to form a 5- to 7-membered ring, alkanesulfonyloxy, arylsulfonyloxy, acylamino, alkylamino or arylamino, or two mutually adjacent substituents $R^{10}$ to $R^{14}$ form one or two further fused ring(s), and
  o is 0 or 1.

In addition, those compounds of the formula I are also preferred in which $R^1$ is a 5- or 6-membered heterocyclic ring having up to three heteroatoms, of the formula III

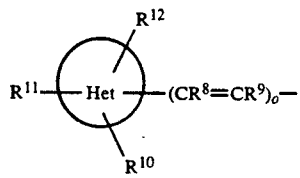

in which $R^8$ to $R^{12}$ and o are defined for formula II.

Finally, those compounds of the formula I are also preferred in which
  $R^1$ is a ferrocenyl radical and $R^2$ is hydrogen, chlorine, bromine, alkyl, cycloalkyl or a radical of the formula II or III, or
  $R^1$ and $R^2$ together form a five- to eight-membered ring,
  $R^3$ is hydrogen or an alkyl radical,
  $R^4$ is hydrogen, halogen, nitro, acylamino, cyano, thiocyanato or an alkyl, aryl, alkylthio, arylthio or cycloalkylthio radical,
  $R^5$ is hydrogen or an alkyl or aryl radical or
  $R^4$ and $R^5$ together form a five- to eight-membered ring,
  $R^6$ is hydrogen, halogen, nitro, acylamino, cyano, thiocyanato or an alkyl, aryl, alkylthio, arylthio or cycloalkylthio radical,
  $R^7$ is an alkyl or cycloalkyl radical, a perfluorinated or highly fluorinated alkyl radical or an aryl, arylalkyl or heteroaryl radical or an alkylene or arylene radical and
  m is 1 or 2 and
  n is 1, 2 or 3.

Those compounds of the formula I are particularly preferred in which $R^7$ is an alkyl radical having 1 to 4 carbon atoms, a highly fluorinated or perfluorinated alkyl radical having 1 to 4 carbon atoms or an aryl radical of the formula IV

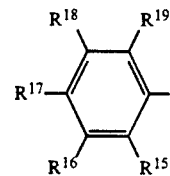

in which $R^{15}$ to $R^{19}$ are identical or different and are hydrogen atoms or halogen atoms, preferably fluorine, chlorine or bromine, alkyl radicals which have up to 6 carbon atoms and are unsubstituted or substituted by halogen atoms, preferably chlorine or bromine, aryl or aryloxy radicals and in which individual methylene groups can be replaced by oxygen or sulfur atoms and in which in each case two of these radicals can be linked to form a 5- or 6-membered ring, cycloalkyl radicals having up to 8 carbon atoms, alkenyl radicals having up to 6 carbon atoms or aryl or aryloxy radicals having up to 10 carbon atoms, the total number of the carbon atoms in the radicals $R^{15}$ to $R^{19}$ being not more than 12.

Those compounds of the formula I are also preferred in which $R^7$ is a naphthyl or heteroaryl radical having up to 10 carbon atoms, an alkylene radical having up to 6 carbon atoms or an arylene or heteroarylene radical having up to 14 carbon atoms.

Those compounds of the formula I are very particularly preferred in which
  $R^2$, $R^3$, $R^4$ and $R^6$ are a hydrogen atom,
  $R^5$ is a methyl group,
  $R^7$ is a methyl, ethyl, trifluoromethyl, 1,1,2,3,3,3-hexafluoropropyl, phenyl, tolyl, 4-fluorophenyl, 4-chlorophenyl, 4-bromophenyl or 4-nitrophenyl radical, and
  m and n are each 1.

According to the present invention, the radical $R^7$ can, for example, be selected from the following: methyl, ethyl, propyl, isopropyl, butyl, hexyl, octyl, decyl, dodecyl, hexadecyl, octadecyl, 10-camphyl, chloromethyl, 2-chloroethyl, 3-chloropropyl, dichloromethyl, trichloromethyl, difluoromethyl, trifluoromethyl, 2,2,2-trifluoroethyl, 3,3,3,2,1,1-hexafluoropropyl, perfluorohexyl, trimethylsilylmethyl, methanesulfonylmethyl, phenyl, benzyl, 4-acetylphenyl, 4-acetylaminophenyl, 2-, 3- or 4-bromophenyl, 2-, 3- or 4-chlorophenyl, 2-, 3- or 4-fluorophenyl, 4-iodophenyl, 2-cyanophenyl, 4-cyanophenyl, 2-, 3- or 4-methylphenyl, 4-ethylphenyl, 4-propylphenyl, 4-isopropylphenyl, 4-isobutylphenyl, 4-tert.-butylphenyl, 4-tert.-amylphenyl, 4-hexylphenyl, 4-methoxyphenyl, 4-butoxyphenyl, 4-hexadecyloxyphenyl, 2-, 3- or 4-trifluoromethylphenyl, 2- or 4-trifluoromethoxyphenyl, 2-, 3- or 4-nitrophenyl, 3- or 4-carboxyphenyl, 2-methoxycarbonylphenyl, 4-tetrafluoroethoxyphenyl, β-styryl, 4-acetylamino-3-chlorophenyl, 4-acetylamino-3-fluorophenyl, 3,5-bistrifluoromethylphenyl, 2,5-bis-(2,2,2-trifluoroethoxy)-phenyl, 2,5-dimethylphenyl, 2,4-, 2,5- or 3,4-dimethoxyphenyl, 2,4-diisopropylphenyl, 5-bromo-2-methoxyphenyl, 2- or 3-chloro-4-fluorophenyl, 3-chloro-2-methylphenyl, 3-chloro-4-methoxyphenyl, 2-chloro-6-methylphenyl, 2-chloro-4-trifluoromethylphenyl, 5-chloro-2-methoxyphenyl, 5-fluoro-2-methylphenyl, 2,5- or 3,4-dibromophenyl, 2,3-, 2,4- 2,5-, 2,6-, 3,4- or 3,5-dichlorophenyl, 2-(2,4-dichlorophenoxy)-phenyl, 4-(2-chloro-6-nitrophenoxy)-phenyl, 4-(3-chloro-2-cyanophenoxy)phenyl, 2,4- or 2,5-difluorophenyl, 3-carboxy-4-chlorophenyl, 4-chloro-3-nitrophenyl, 2-methyl-5-nitrophenyl, 4-chloro-3- or 2-chloro-5-trifluoromethylphenyl, 4-(2,2-dichlorocyclopropyl)-phenyl, 2,4-dinitrophenyl, 4-dimethylamino-3-nitrophenyl,2-nitro-4-trifluoromethylphenyl, 2,4,6-trimethylphenyl, 2,4,6-triisopropylphenyl, 2,3,4-, 2,4,5- or 2,4,6-trichlorphenyl, 4-chloro-2,5-dimethylphenyl, 2,4-dichloro-5-methylphenyl, 3,5-dichloro-2-hydroxyphenyl, 3,5-dichloro-4-(4-nitrophenoxy)-phenyl, 4-(2-chloro-4-nitrophenoxy)-3,5-dichlorophenyl,4-bromo-2,5-difluorophenyl, 2,4-dimethyl-3-nitrophenyl, 3,5-dinitro-4-methylphenyl, 2,3,5,6-tetramethylphenyl, 4-methoxy-2,3,6-trimethylphenyl, 2,5-dibromo-3,6-difluorophenyl, 2,3,4,5,6-pentafluorophenyl, 1- or 2-naphthyl, 5-diazo-6-oxo-5,6-dihydro-1-naphthyl,6-diazo-5-oxo-5,6-dihydro-1-naphthyl,5-diazo-6-oxo-5,6-dihydro-8-naphthyl, 5-diazo-3-methoxy-6-oxo-5,6-dihydro-8-naphthyl, 5-dimethylamino-1-naphthyl, 1-anthracenyl, 2-anthraquinonyl, 8-quinolinyl, 2-thienyl, 5-chloro-2-thienyl, 4-bromo-2,5-dichloro-3-thienyl, 4,5-dibromo-2-thienyl, 2,3-dichloro-5-thienyl, 2-bromo-3-chloro-5-thienyl, 3-bromo-2-chloro-5-thienyl, 3-bromo-5-chloro-2-thienyl, 2,5-dichloro-3-thienyl, 2-(2-pyridyl)-5-thineyl, 5-chloro-1,3-dimethyl-4-pyrazolyl, 3,5-dimethyl-4-isoxazolyl, 2,4-dimethyl-5-thiazolyl, 2-acetylamino-4-methyl-5-thiazolyl, 1,4-butylene, 2-oxo-1,3-propylene, 1,2- or 1,3-phenylene, 3-methyl-1,2-phenylene, 2,4,6-trimethyl-1,3-phenylene, 4,4'-biphenylene, 4,4'-methylenediphenylene, 4,4'-oxybiphenylene, 1,5-naphthylene, 2-chloro-3,5-thienylene, 2-(1-methyl-5-trifluoromethylpyrazol-3-yl)-3,5-thienylene.

According to the present invention, the radical $R^1$ can, for example, be selected from the following: methyl, chloromethyl, bromomethyl, ethyl, propyl, isopropyl, butyl, isobutyl, hexyl, cyclohexyl, octyl, phenyl, 4-acetylaminophenyl, 4-acetoxyphenyl, 3- or 4-benzyloxyphenyl, 3-benzyloxy-4-methoxyphenyl, 4-benzyloxy-3-methoxyphenyl, 4-biphenyl, 3,5-bis(trifluoromethyl)-phenyl, 2-, 3- or 4-fluorophenyl, 2-, 3- or 4-chlorophenyl, 2-, 3- or 4-bromophenyl, 4-iodophenyl, 2-, 3- or 4-cyanophenyl, 2-, 3- or 4-methylphenyl, 2-, 3 or 4-ethylphenyl, 2-, 3- or 4-propylphenyl, 2-, 3- or 4-isopropylphenyl, 2-, 3- or 4-butylphenyl, 2-, 3- or 4-isobutylphenyl, 2-, 3- or 4-sec.-butylphenyl, 2-, 3- or 4-tert.-butylphenyl, 2-, 3- or 4-pentylphenyl, 2-, 3- or 4-hexylphenyl, 2-, 3- or 4-cyclohexylphenyl, 2-, 3- or 4-nonylphenyl 2-, 3- or 4-dodecylphenyl, 2-, 3- or 4-methoxyphenyl, 2-, 3- or 4-ethoxyphenyl, 2-, 3- or 4-isopropoxyphenyl, 2-, 3- or 4-butoxyphenyl, 2-, 3- or 4-pentoxyphenyl, 2-, 3- or 4-octyloxyphenyl, or 2-, 3- or 4-decyloxyphenyl, 2,3-, 2,4-, 2,6-, 3,4- or 3,5-difluorophenyl, 2,3-, 2,4-, 2,6-, 3,4- or 3,5-dichlorophenyl, 2,3-, 2,4-, 2,6-, 3,4- or 3,5-dibromophenyl, 3-(3,4-dichlorophenoxy)-phenyl, 3-(3,5-dichlorophenoxy)-phenyl, 3-bromo-4-fluorophenyl, 5-bromo-2,4-dimethoxyphenyl, 2-chloro-6-fluorophenyl, 2-chloro-5-,2-chloro-6-,4-chloro-3- or 5-chloro-2-nitrophenyl, 3-(4-chlorophenoxy)-phenyl, 3,4-bisbenzyloxyphenyl, 2,3-, 2,4-, 2,5-, 3,4- or 3,5-dimethoxy-phenyl, 2,3-, 2,4-, 2,5-, 3,4- or 3,5-diethoxy-phenyl, 2,3-, 2,4-, 2,5-, 3,4- or 3,5-dibutoxy-phenyl, 2,3-, 2,4-, 2,5-, 3,4- or 3,5-dihexyloxy-phenyl, 2,4-dimethoxy-3-methyl-phenyl, 2-ethoxy-5-methoxy-phenyl, 3-chloro-4-methyl-phenyl, 2,4- or 2,5-dimethylphenyl, 2-, 3- or 4-methoxyethyl-phenyl, 2-, 3- or 4-ethoxyethyl-phenyl, 2-, 3- or 4-butoxyethylphenyl, 2,6-dinitro-phenyl, 2,4,6-trimethylphenyl, 3,4,5-trimethoxy-phenyl, 3,4,5-triethoxy-phenyl, 2,3- or 3,4-methylenedioxyphenyl, 2- or 3-thienyl, 2-fluorenyl, 9-anthryl, 1-pyrenyl, 9-phenanthryl, 5-bromo-2-thienyl, 3-methyl-2-thienyl, 5-methyl-2-thienyl, 5-nitrofuryl, 10-chloro-9-anthryl or ferrocenyl.

These radicals for $R^1$ and $R^7$ are preferred particularly for the reason that the starting compounds on which they are based are commercially available. However, further compounds can be prepared in a simple manner by methods familiar to those skilled in the art and hence other $R^1$ and $R^7$ radicals can be used, so long as they fall within formula I of the invention.

Under the action of actinic radiation, the compounds I form reactive intermediates which are capable of initiating specific chemical reactions, for example free-radical polymerizations. When irradiated, however, they generate organic acids which catalyze reactions, such as cationic polymerizations, crosslinking reactions or cleavage of acid-unstable compounds, or can react with bases, resulting in, for example, a color change of indicator dyes.

The compounds listed above have absorption maxima in the range between 200 and 550 nm and are therefore very well suitable for irradiation with high-energy UV radiation in the range of UV2 radiation (220 to 280 nm), UV3 radiation (300 to 350 nm) or UV4 radiation (350 to 450 nm) and also with high-energy visible light (450 to 550 nm). They show high activities even on irradiation with radiation of a wavelength of <220 nm; however, because of their high absorption in this region, they are preferentially applicable to so-called "toplayer imaging" processes.

The invention also relates to a process for preparing the novel chromophorically substituted I-sulfonyloxy-2pyridones of the formula I. A specific example of such a process is illustrated below.

$$H-CH_2-\underset{\underset{CH_3}{|}}{C}=CH-\overset{O}{\overset{\|}{C}}-O-CH_3 + Cl-CH_2-\overset{O}{\overset{\|}{C}}-Cl \xrightarrow{AlCl_3}$$

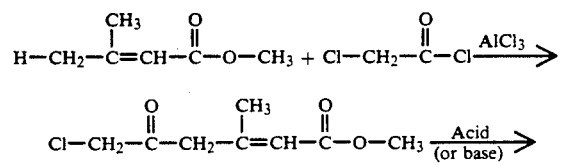

$$Cl-CH_2-\overset{O}{\overset{\|}{C}}-CH_2-\underset{\underset{CH_3}{|}}{C}=CH-\overset{O}{\overset{\|}{C}}-O-CH_3 \xrightarrow[\text{(or base)}]{\text{Acid}}$$

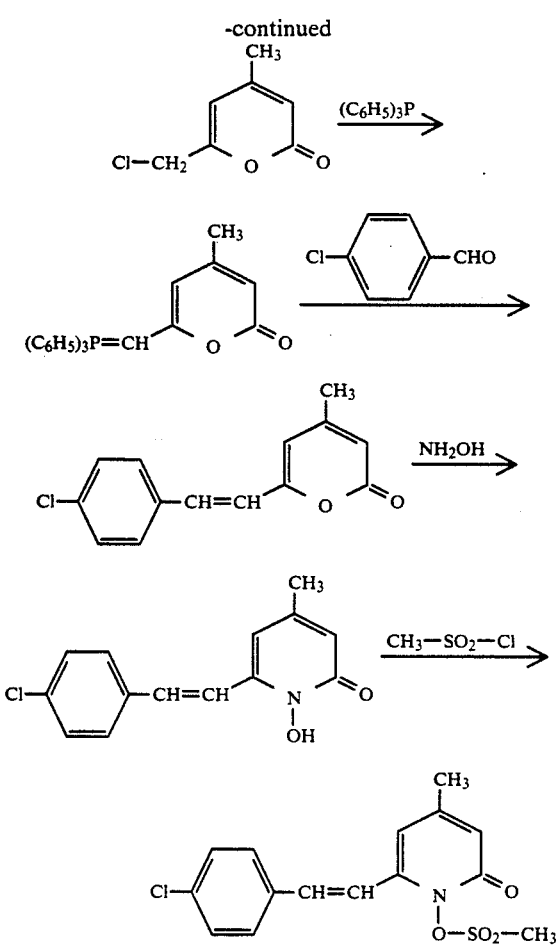

As seen from the diagram, the process involves the following steps a) a 6-halogenomethyl-2-pyrone is converted into a phosphonium compound or phosphono compound,
b) the latter is subjected to a Wittig reaction or variants thereof,
c) the resulting compound is converted into a 1-hydroxy-2-pyridone by reaction with hydroxylamine, and
d) reacted with a sulfonic acid halide to give a 1-sulfonyloxy-2-pyridone of the formula I.

The sulfonic acid halide used is preferably a sulfonic acid chloride. The reaction with the sulfonic acid halide is expediently carried out in the presence of an organic base in an organic solvent at temperatures between 0° and 20° C.

The novel chromophorically substituted 1-sulfonyloxy-2-pyridones of the formula I can be used in an outstanding manner as photoinitiators or photo-acid generators for radiation-sensitive recording materials. Their use in positive- and negative-working radiation-sensitive mixtures is explained in the application examples 1 to 4 described below; a detailed description of their possible uses is given in Ser. Nos. 07/871,027 and 07/871,007, which respectively correspond to German Patent Applications P 41 12 966.0 and P 41 12 965.2, filed concomitantly, both of which are hereby incorporated by reference in their entireties.

The examples described below illustrate the invention, but they are not intended to effect a restriction. In the following text, p.b.w. means parts by weight and p.b.v. means parts by volume, which has the same relationship to parts by weight as does g to cm$^3$.

PREPARATION EXAMPLES

Examples 1 to 5 illustrate the preferred methods for preparing the chromophorically substituted 1-sulfonyloxy-2-pyridones of the formula I, (compounds 1-5) according to the invention. It is readily evident to those skilled in the art that these preparation methods can also be applied to the compounds 6 to 109 and that even this selection does not yet represent a limitation of the concept of the invention. By reference to Application Examples 1 to 4, a few typical possible applications of the compounds of the formula I according to the invention are illustrated. In the first preparation example, the complete synthesis route,, starting from raw materials available on a large industrial scale, is described. Detailed reports of the first stages of this synthesis have already been given by G. Lohaus et al., Chem. Ber., 100, 658, 1967. A large number of 1-hydroxy-2-pyridones substituted in different ways and methods for their preparation have been described in Arzneim. Forsch./Drug Res., 31 (II), 8a, 1311, (1981).

PREPARATION EXAMPLE 1

1st Stage: 230 p.b.w. of methyl 3-methylcrotonate was added at 50° to 60° C. to a suspension of 532 p.b.w. of aluminum trichloride in 250 p.b.v. of ethylene chloride and 282 p.b.w. of chloroacetyl chloride in such a way that the temperature was just held constant. The mixture was then heated for one hour to 65° to 70° C. and poured onto ice. The aqueous phase was extracted with methylene chloride and the organic phase was washed with water and saturated sodium hydrogen carbonate solution. After drying over sodium sulfate, the product was fractionally distilled. Yield: 280 p.b.w. (74%), boiling point 120° to 122° C./5 mm Hg.

2nd Stage: 382 p.b.w. of the product described above was dissolved in a mixture of 1000 p.b.v. of glacial acetic acid and 10 p.b.v. of concentrated sulfuric acid, and the solution was heated to boiling. The calculated quantity of methyl acetate was distilled off through a short column. The glacial acetic acid was then removed in vacuo and the residue was poured into ice water, resulting in the pyrone crystallizing. For further purification, the product separated off can be distilled at 116° to 117° C./2 mm Hg. After recrystallization from carbon tetrachloride, this gave 296 p.b.w. of 6-chloromethyl-4-methyl-2-pyrone. Yield: 93%, melting point 78° C.

3rd Stage: 320 p.b.w. of the product described above was heated under reflux for 8 hours together with 540 p.b.w. of triphenylphosphine and 1500 p.b.v. of acetonitrile. The mixture was cooled in ice and the precipitated product was filtered off with suction. The mother liquor was concentrated and further product precipitated which was filtered off with suction. This gave 799 p.b.w. of (4-methyl-6-oxo-6H-pyron-2-ylmethyl)triphenyl-phosphonium chloride.

4th Stage: 106 p.b.w. of the product described above was dissolved in 200 p.b.v. of methanol together with 35.5 p.b.w. of 4-chlorobenzaldehyde. A solution of 6 p.b.w. of sodium in 150 p.b.v. of methanol was poured into the solution. The mixture assumed a transient red color and reacted highly exothermically. The mixture was stirred for 6 hours at room temperature and cooled to −25° C. The precipitated product was filtered off with suction, washed with cooled methanol, stirred with water and again filtered with suction. This gave 26 p.b.w. of 6-(4-chlorostyryl)-4-methyl-2-pyrone, which can be recrystallized from acetonitrile, and has a melting point of 144° C.

5th Stage: 22.5 p.b.w. of the product described above was heated to about 70° C. with 9 p.b.w. of hydroxylamine hydrochloride and 110 p.b.w. of 2-aminopyridine. The mixture was left for 72 hours at this temperature, and a further 3.3 p.b.w. of hydroxylamine hydrochloride being added each time after 3, 18, 30 and 42 hours. After the mixture was cooled, it was taken up in methylene chloride and washed with dilute hydrochloric acid and water. The organic phase was stirred up in a solution of 10 p.b.w. of sodium hydroxide in 700 p.b.v. of deionized water, and the resulting sodium salt was filtered off and dissolved in 600 p.b.v. of hot water. The aqueous solution was adjusted to pH 5 by addition of glacial acetic acid and cooled down. The crude product thus crystallizing was filtered off with suction and dried. This gave 15 p.b.w. of a crude product having a melting point of 195° C., which was recrystallized from methylene chloride. This gave yellowish crystals of [6-(4-chlorostyryl)-1-hydroxy-4-methyl-2-pyridone] having a melting point of 205° C.

Analysis: calculated: C, 64.25%; H, 4.62%; N, 5.35%. (261.70) found: C, 64.2%; H, 4.6%; N, 5.4%.

6th Stage: 1.85 p.b.w. of triethylamine in 20 p.b.v. of methylene chloride was added dropwise at 10° C. to a solution of 4 p.b.w. of the product described above and 20 p.b.w. of methanesulfonyl chloride in 50 p.b.v. of methylene chloride. The solution was stirred at room temperature for 24 hours and extracted by shaking with water. The solvent was removed in a rotary evaporator. The crystalline product was dried, passed on a silica gel column and eluted with methylene chloride. The combined product fractions gave, after concentrating, 4.2 p.b.w. of 6-(4-chlorostyryl)-1-methanesulfonyloxy-4-methyl-2-pyridone having a decomposition point of 190° C. A sample was recrystallized from acetonitrile and gave a product having a decomposition point of 193° C.

Analysis: calculated: C, 53.02%; H, 4.15%; N, 4.12%. (339.77) found: C, 52.7%; H, 4.4%; N, 4.2%.

PREPARATION EXAMPLE 2

1st Stage: 108 p.b.w. of triethyl phosphite was slowly added dropwise with stirring at 100° C. in a distillation apparatus to 79.3 p.b.w. of 6-chloromethyl-4-methyl-2-pyrone (see Preparation Example 1, 2nd Stage). At this stage, ethyl chloride distilled over into the receiver. When the elimination of ethyl chloride subsided, the bath temperature was slowly increased to 130° C. and the mixture was stirred for about a further 6 hours at this temperature. After this time, a further 320 p.b.w. of 6-chloro-methyl-4-methyl-2-pyrone was added to the mixture, and 432 p.b.w. of triethyl phosphite was slowly added dropwise at a bath temperature of 140° C. The mixture was again stirred at this temperature for a further 9 hours. After cooling, volatile constituents of the mixture were then subsequently distilled off in the course of about 3 hours at 70° C. in the vacuum of an oil pump. 610 p.b.w. of 6-diethoxy-phosphorylmethyl-4-methyl-2-pyrone remained as a viscous residue, which started to crystallize after some time.

2nd Stage: 7.75 p.b.w. of sodium hydride (80% suspension) was added under inert gas and with intensive stirring to a mixture of 45.5 p.b.w. of benzophenone, 65 p.b.w. of the compound described above and 200 p.b.v. of 1,2-dimethoxyethane. The mixture was stirred for 24 hours at 70° C., taken up in methylene chloride, washed several times with water, dried and concentrated in a rotary evaporator. This gave 74.3 p.b.w. of a crude product which contained two components and was separated over a silica gel column with methylene chloride as the solvent. The fractions containing the product with the higher retention time were combined and concentrated. This gave 55 p.b.w. of crystalline 6-(2,2-diphenylvinyl)-4-methyl-2-pyrone, which can be recrystallized from hexane.

3rd Stage: 20 p.b.w. of the product described above was heated with 5.6 p.b.w. of hydroxylamine hydrochloride and 80 p.b.w. of aminopyridine to about 75° C. The mixture was left at this temperature for 58 hours, a further 2.8 p.b.w. of hydroxylamine hydrochloride being added each time after 6, 22 and 32 hours. After the mixture was cooled, it was taken up in methylene chloride and washed with dilute hydrochloric acid and water, dried and concentrated. The resulting residue, 22 p.b.w., was recrystallized from acetonitrile. This gave 14 p.b.w. of a yellow product [6-(2,2-diphenyl-vinyl)-1-hydroxy-4-methyl-2-pyridone] having a melting point of 169° C.

Analysis: calculated: C, 79.18%; H, 5.65%; N, 4.62%. (303.26) found: C, 79.0%; H, 5.8%; N, 4.5%.

4th Stage: 3 p.b.w. of triethylamine in 20 p.b.v. of methylene chloride was added dropwise at 5° to 10° C. to a solution of 8 p.b.w. of the product described above and 3.5 p.b.w. of methanesulfonyl chloride in 70 p.b.v. of methylene chloride. The mixture was stirred for a further 24 hours at room temperature, and extracted with water by shaking. The solvent was removed in a rotary evaporator. The viscous residue amounting to about 12.5 p.b.w. crystallized when left standing and had a melting point of about 130° C. The crude product was eluted with methylene chloride over a silica gel column. After concentrating, the combined product fractions gave 8.2 p.b.w. of 6-(2,2-diphenyl-vinyl)-1-methanesulfonyloxy-4-methyl-2-pyridone having a melting point of 140° C.

Analysis: calculated: C, 66.12%; H, 5.02%; N, 3.67%. (381.44) found: C, 65.7%; H, 5.1%; N, 3.4%.

PREPARATION EXAMPLE 3

Stage 1: 85 p.b.w. of (4-methyl-6-oxo-6H-pyron-2-yl-methyl)-triphenyl-phosphonium chloride (see Preparation Example 1, 3rd Stage) and 41.2 p.b.w. of anthracene 9-carbaldehyde were dispersed in 200 p.b.v. of methanol. A solution of 5 p.b.w. of sodium in 100 p.b.v. of methanol was added fairly rapidly with stirring to the dispersion, causing the mixture to warm up. This was stirred for 1 hour at about 50° C. and then for a further 72 hours at room temperature. The mixture was subsequently cooled down to −25° C., and the precipitated product was filtered off with suction. The product was washed with methanol, then stirred with water and again filtered off with suction. This gave 52 p.b.w. of 6-(2-anthracene-9-yl-vinyl)-4-methyl-2-pyrone having a melting point of about 200° C., which had a melting point of 203° C. when recrystallized from acetonitrile.

Stage 2: 20 p.b.w. of the pyrone described above was heated to 70° C. with 5.6 p.b.w. of hydroxylamine hydrochloride and 80 p.b.w. of 2-aminopyridine. The mixture was left for 72 hours at this temperature, a further 2.8 p.b.w. of hydroxylamine hydrochloride being added each time after 7, 23 and 32 hours. After the mixture was cooled, it was taken up in methylene chloride and washed with dilute hydrochloric acid and water. A part of the product thus precipitated. The organic phase was concentrated in a rotary evaporator and the residue was recrystallized from dimethylformamide (DMF). The crystals obtained were, together with the precipitated product, again recrystallized from DMF and washed with methanol. This gave 12.6 p.b.w. of an analytically pure orange-colored powder [6-(2-anthracene-9-yl-vinyl)-1-hydroxy-4-methyl-2-pyridone] which had a melting point of >260° C.

Analysis: calculated: C, 80.71%; H, 5.24%; N, 4.28%. (327.39) found: C, 80.9%; H, 5.4%; N, 4.3%.

3rd Stage: 4.5 p.b.w. of the compound described above and 1.83 p.b.w. of methanesulfonyl chloride were dissolved in 50 p.b.v. of methylene chloride, and the solution was cooled to 5° C. A mixture of 1.6 p.b.w. of triethylamine in 20 p.b.v. of methylene chloride was slowly added dropwise to the solution. The mixture was stirred for a further 3 days at room temperature. The organic phase was washed with water and dried, and the solvent was stripped off in a rotary evaporator. The residue was again taken up in methylene chloride and eluted over a silica gel column with methylene chloride as the solvent. The clearly identifiable main fraction was collected and freed of solvent, and the remaining foam-like product was stirred with warm diisopropyl ether. After drying, this gave 1.9 p.b.w. of 6-(2-anthracene-9-yl-vinyl)-1-methanesulfonyloxy-4-methyl-2-pyridone which decomposed at a temperature of 180° C. with deflagration.

Analysis: calculated: C, 68.13%; H, 4.72%; N, 3.46%. (405.48) found: C, 68.1%; H, 4.9%; N, 3.3%.

PREPARATION EXAMPLE 4

Stage 1: 26 p.b.w. of 6-diethoxyphosphorylmethyl-4-methyl-2-pyrone (see Preparation Example 2, 1st Stage) and 17.4 p.b.w. of 4-trifluoromethylbenzaldehyde were dissolved in 80 p.b.v. of 1,2-dimethoxyethane. Under nitrogen, 3.2 p.b.w. of an 80% sodium hydride dispersion was then added in portions in such a way that the reaction mixture did not heat up to more than 50° C. It was stirred for a further 18 hours at this temperature and, after cooling, diluted with methylene chloride. The solution was washed several times with water, dried and concentrated. 26.9 p.b.w. of a crystalline powder remained which was eluted over a silica gel column with methylene chloride as the solvent. After concentrating, the main fraction gave 18.9 p.b.w. of a powder of melting point 155° C,, which proved to be the desired analytically pure 4-methyl-6-(4-trifluoromethyl-styryl)-2-pyrone.

Stage 2: 15 p.b.w. of the product described above, 45 p.b.w. of imidazole, 5 p.b.w. of N-methylpyrrolidone and 5.6 p.b.w. of hydroxylamine hydrochloride were heated for 55 hours at 75° C. with stirring. A further 2.8 p.b.w. of hydroxylamine hydrochloride was added each time after 8, 24 and 32 hours of reaction time. After the mixture was cooled, it was taken up in methylene chloride, washed with water, dried and concentrated. This gave 14.6 p.b.w. of a crude product which was recrystallized from ethylene glycol monomethyl ether. The 1-hydroxy-methyl-6-(4-trifluoromethyl-styryl)-2-pyridone which had crystallized out showed a melting point of 230° C.

Analysis: calculated: C, 61.02%; H, 4.10%; F, 19.30%; N, 4.74%. (295.28) found: C, 61.3%; H, 4.1%.

Stage 3: 1.8 p.b.w. of the compound described above and 1.9 p.b.w. of 4-bromobenzenesulfonyl chloride were dissolved in 40 p.b.v. of methylene chloride and the solution was cooled to 5° C. A mixture of 1.0 p.b.w. of triethylamine in 5 p.b.v. of methylene chloride was slowly added dropwise to the solution. Stirring was continued for a further 66 hours at room temperature. The organic phase was washed with water and dried, and the solvent was stripped off in a rotary evaporator. The residue (3.2 p.b.w.) was again taken up in methylene chloride and eluted over a silica gel column with methylene chloride/methanol (99/1) as the solvent. The clearly identifiable main fraction was collected and freed of solvent, and the remaining foam-like product was stirred with warm diisopropyl ether, crystallization of the product taking place. After drying, this gave 2.2 p.b.w. of 1-(4-bromobenzenesulfonyloxy)-4-methyl-6-(4-trifluoromethyl-styryl)-2-pyridone which melted at a temperature of 158° C.

Analysis: calculated: C, 49.04%; H, 2.94%; N, 2.72%; F, 11.08%. (514.33) found: C, 48.6%; H, 3.1%; N, 2.7%.

PREPARATION EXAMPLE 5

Stage 1: 32.5 p.b.w. of 6-diethoxyphosphorylmethyl-4-methyl-2-pyrone (see Preparation Example 2, 1st stage) and 30 p.b.w. of 4-(4-chlorophenylmercapto)-benzaldehyde were dispersed in 120 p.b.v. of methanol. A solution of 3.1 p.b.w. of sodium in 120 p.b.v. of methanol was added dropwise under nitrogen. The mixture reacted exothermically and, after brief formation of a clear solution, a voluminous precipitate was formed. The mixture was stirred for a further 22 hours at room temperature, cooled with ice and filtered with suction. The residue, virtually analytically pure, was washed with prechilled methanol and dried. This gave 35 p.b.w. of 6-[4-(4-chlorophenylmercapto)styryl]-4-methyl-2-pyrone which melted at 164° C.

Stage 2: 20 p.b.w. of the product described above, 80 p.b.w. of 2-aminopyridine and 5.6 p.b.w. of hydroxylamine hydrochloride was heated with stirring at 75° C. for 83 hours. A further 2.8 p.b.w. of hydroxylamine hydrochloride were added each time after 18, 27 and 34 hours of reaction time. After the mixture was cooled, it was taken up in methylene chloride and washed with dilute hydrochloric acid and water, dried and concentrated. This gave 21.8 p.b.w. of a crude product which was recrystallized from ethylene glycol monomethyl ether. The 6-[4-(4-chloro-phenylmercapto)styryl]-1-hydroxy-4-methyl-2-pyrone which had crystallized out showed a melting point of 210° C.

Analysis: calculated: C, 64.95%; H, 4.36%; Cl, 9.58%; N, 3.79%. (369.88) found: C, 65.1%; H, 4.5%.

Stage 3: 3.45 p.b.w. of the compound described above and 2.15 p.b.w. of 4-fluorobenzenesulfonyl chloride were dissolved in 40 p.b.w. of methylene chloride and the solution was cooled to 5° C. A mixture of 1.3 p.b.w. of triethylamine in 10 p.b.v. of methylene chloride was slowly added dropwise to the solution. Stirring was continued for a further 66 hours at room temperature. The organic phase was washed with water and dried, and the solvent was stripped off in a rotary evaporator. The viscous residue (5.1 p.b.w.) was again taken up in methylene chloride and eluted over a silica gel column with methylene chloride/methanol (99/1) as the solvents. The clearly identifiable main fraction was collected and freed of solvent, and the remaining foam-like product was stirred with warm diisopropyl ether, with microcrystallization of the product taking place. The product was recrystallized from acetonitrile. After drying, this gave 2.0 p.b.w. of 6-[4-(4-chlorophenylmercapto)-styryl]-1-(4fluorobenzenesulfonyloxy)-4-methyl-2-pyridone which had a melting point of 150° C.

Analysis: calculated: C, 59.14%; H, 3.63%; N, 2.65%; F, 3.60%. (528.03) found: C, 59.2%; H, 3.7%; N, 2.6%.

COMPOUNDS 6 TO 109

Further compounds according to the invention, which can be prepared correspondingly to the preparation examples described above, are listed below:

6) 6-(4-fluoro-styryl)-1-methanesulfonyloxy-4-methyl-2-pyridone
7) 1-benzenesulfonyloxy-4-methyl-6-styryl-2-pyridone
8) 6-(3,4-dimethoxy-styryl)-1-ethanesulfonyloxy-4-methyl-2-pyridone
9) 6-(4-methoxy-styryl)-4-methyl-1-(4-nitrobenzenesulfonyloxy)-2-pyridone
10) 6-(4-cyano-styryl)-4-methyl-1-trifluoromethanesulfonyloxy-2-pyridone
11) 6-(3-benzyloxy-styryl)-1-(4-chlorobenzenesulfonyloxy)-4-methyl-2-pyridone
12) 1-butanesulfonyloxy-6-(3,4-dichloro-styryl)-4-methyl-2-pyridone
13) 1-(4-chloro-3-nitro-benzenesulfonyloxy)-6-(3-ethoxy-6-methoxy-styryl)-4-methyl-2-pyridone
14) 1-(4-bromo-benzenesulfonyloxy)-6-(3-chloro-4-methylstyryl)-4-methyl-2-pyridone
15) 6-(4-benzyloxy-3-methoxy-styryl)-1-(4-chlorobenzenesulfonyloxy)-4-methyl-2-pyridone
16) 1-isopropanesulfonyloxy-6-(4-phenyl-buta-1,3-dienyl)-4-methyl-2-pyridone
17) 4-methyl-6-(2-naphthalen-1-yl-vinyl)-1-(3-nitrobenzenesulfonyloxy)-2-pyridone
18) 6-[4-(2-ethoxy-ethoxy)-styryl]-1-methanesulfonyloxy-4-methyl-2-pyridone
19) 6-(2,4-dimethoxy-3-methyl-styryl)-1-(toluene-4-sulfonyloxy)-4-methyl-2-pyridone
20) 4-methyl-6-styryl-1-trichloromethanesulfonyloxy-2-pyridone
21) 4-methyl-6-(2-naphthalen-2-yl-vinyl)-1-(toluene-4-sulfonyloxy)-2-pyridone
22) 4-cyclohexyl-1-methanesulfonyloxy-6-(4-methoxystyryl)-2-pyridone
23) 3-cyano-6-(3,4-dimethoxy-styryl)-4-methyl-1-(toluene-4-sulfonyloxy)-2-pyridone
24) 6-[2-(4-chloro-phenyl)-prop-1-enyl]-1-methanesulfonyloxy-4-methyl-2-pyridone
25) 6-(3-chloro-4-methoxy-styryl)-1-(4-nitrobenzenesulfonyloxy)-4-phenyl-2-pyridone
26) 4-butyl-6-(3,4-dimethoxy-styryl)-1-(4-methoxybenzenesulfonyloxy)-2-pyridone
27) 6-[2,2-bis-(4-methoxy-phenyl)-vinyl]-4-methyl-1-(toluene-4-sulfonyloxy)-2-pyridone
28) 6-(2-anthracen-9-yl-vinyl)-4-methyl-1-(toluene-4-sulfonyloxy)-2-pyridone
29) 1-benzenesulfonyloxy-5-chloro-4-ethyl-6-(4-methoxystyryl)-2-pyridone
30) 4-methyl-3-nitro-6-(2-thiophen-2-yl-vinyl)-1-(toluene-4-sulfonyloxy)-2-pyridone
31) 3-butylmercapto-1-methanesulfonyloxy-6-(4-methoxystyryl)-4-methyl-2-pyridone
32) 3,5-dibromo-4-methyl-6-(3-methyl-styryl)-1-(toluene-4-sulfonyloxy)-2-pyridone
33) 1-ethanesulfonyloxy-3-methoxymethyl-4-methyl-6-(2-naphthalen-2-yl-vinyl)-2-pyridone
34) 3,5-dichloro-6-(2-(6-methoxy-naphthalen-2-yl)vinyl]-4-methyl-1-(toluene-4-sulfonyloxy)-2-pyridone
35) 1-methanesulfonyloxy-4-methyl-6-(4-phenyl-styryl)2-pyridone
36) 1-benzenesulfonyloxy-3-bromo-6-[4-(4-chloro-phenoxy)-styryl]-4-methyl-2-pyridone
37) 6-[4-(4-chloro-phenylmercapto)-styryl]-1-(4-fluorobenzenesulfonyloxy)-4-methyl-2-pyridone
38) 6-[4-(4-chloro-benzyloxy)-styryl ]-1-(4-isopropyl-benzenesulfonyloxy)-4-methyl-2-pyridone
39) 6-(4-chloro-3-trifluoromethyl-styryl)-1-(1,1,2,3,3,3-hexafluoropropanesulfonyloxy)4-methyl-2-pyridone
40) 1-benzenesulfonyloxy-6-(4-dimethylamino-styryl)4-methyl-2-pyridone
41) 6-(4-allyloxy-styryl)-1-methanesulfonyloxy-4-methyl-2-pyridone
42) 6-(3,5-dichloro-4-hexyloxy-styryl)-4-methyl-1-propanesulfonyloxy-2-pyridone
43) 4-methyl-6-(2-phenyl-2-cyclohexyl-vinyl)-1-(toluene-4-sulfonyloxy)-2-pyridone
44) 1-(4-methoxy-benzenesulfonyloxy)-4-methyl-6-(2-phenyl-hex-1-enyl)-2-pyridone
45) 3-bromo-6-(2-cyclohexyl-vinyl)-4-methyl-1-trifluoromethanesulfonyloxy)-2-pyridone
46) 4-ethyl-1-methanesulfonyloxy-6-pent-1-enyl-2-pyridone
47) 1-methanesulfonyloxy-4-methyl-6-(2-methyl-propenyl)-2-pyridone
48) 6-cyclooctylidenemethyl-1-methanesulfonyloxy-4-methyl-2-pyridone
49) 6-cyclopentylidenemethyl-4-methyl-1-(toluene-4-sulfonyloxy)-2-pyridone
50) 6-[2-(5-bromo-thiophen-2-yl]-vinyl]-3-methanesulfonylamino-1-methanesulfonyloxy-4-methyl-2-pyridone
51) 6-(2-(5-bromo-thiophen-2-yl)-vinyl]-3-isobutyryl amino-4-methyl-1-(toluene-4-sulfonyloxy)-2-pyridone
52) 1-ethanesulfonyloxy-6-(2-methyl-6-phenyl-hexa-1,3,5-trienyl)-4-methyl-2-pyridone
53) 6-(4-cyclohexyloxy-styryl)-1-(1,1,2,3,3,3-hexafluoro-propanesulfonyloxy)-4-methyl-2-pyridone
54) 6-(3 -cyclopropyloxy-styryl)-1-methanesulfonyloxy-4-methyl-2-pyridone
55) 6-(2-benzofuran-2-yl-vinyl)-4-methyl-1-(toluene-4-sulfonyloxy)-2-pyridone
56) 6-[2-(5-bromo-thiophen-2-yl)-vinyl]-4-methyl-1-(3-trifluoromethyl-benzenesulfonyloxy)-2pyridone
57) 4-methyl -6-[2-(5-methyl-furan-2-yl)-vinyl]-1-(naphthalen-2-ylsulfonyloxy)-2pyridone
58) 4-methyl-6-(4-nitro-styryl)-1-octanesulfonyloxy-2-pyridone
59) 1-hexadecanesulfonyloxy-4-methyl-6-(4-nitrostyryl)-2-pyridone
60) 1-methanesulfonyloxy-4-methyl-6-(4-nitro-styryl)2-pyridone
61) 6-(2,2-di-thiophen-2-yl-vinyl)-1-methanesulfonyloxy-4-methyl-2-pyridone
62) 3-cyano-6-(2,4-dimethoxy-styryl)-4-methyl-1-trifluoromethanesulfonyloxy-2-pyridone
63) 6-(2-benzofuran-2-yl-vinyl)-4-methyl-3-thiocyanato-1-(toluene-4-sulfonyloxy)-2-pyridone
64) 6-(2-benzofuran-2-yl-vinyl)-3-bromo-1-methanesulfonyloxy-4-methyl-2-pyridone
65) 3,5-bis-isopropylmercaptomethyl-4-methyl-1-(4-nitro-benzenesulfonyloxy)-6-styryl-2-pyridone
66) 1-(4-methoxy-benzenesulfonyloxy)-4-methyl-6-(2,3,4,5,6-pentafluoro-styryl)-2-pyridone 67) 6-(3,5-dichloro-2,4,6-trimethoxy-styryl)-4-methyl-1-(1-trifluoromethyl-2,2,2-trifluoro-ethanesulfonyloxy)-2-pyridone
68) 6-(3-bromo-2,4,6-trimethoxy-styryl)-1-methanesulfonyloxy-4-methyl-2-pyridone
69) 6-(2-ferrocenyl-vinyl)-4-methyl-1-(toluene-4-sulfonyloxy)-2-pyridone
70) 6-[2-(5-methyl-furan-2-yl)-vinyl]-4-methyl-3-nitro-1-(toluene-4-sulfonyloxy)-2-pyridone
71) 6-(4-tert.-butyl-styryl)-4-methyl-5-nitrolpropanesulfonyloxy-2-pyridone
72) 3,5-dinitro-6-(4-tert.-butyl-styryl)-4-methyl-1-butanesulfonyloxy-2-pyridone
73) 1-benzenesulfonyloxy-3-bromo-6-(4-butoxy-styryl)-4-methyl-5-nitro-2-pyridone
74) 1-(4-bromo-benzenesulfonyloxy)-4-methyl-6-(4-trifluoromethyl-styryl)-2-pyridone
75) 6-(3-chloro-5-phenyl-buta-1,3-dienyl)-1-isopropanesulfonyloxy-4-methyl-2-pyridone
76) 1-benzenesulfonyloxy-4-methyl-6[2-(1-benzenesulfonyl-pyrrol-2-yl)-vinyl]-2-pyridone
77) 6-(10,11-dihydro-dibenzo[a,d]cyclohept-5-ylidenemethyl)-4-methyl-1-(2-thiophen-2-ylsulfonyloxy)-2-pyridone
78) 1-benzenesulfonyloxy-4-methyl-6-(4-styryl-styryl)2-pyridone
79) 1-methanesulfonyloxy-4-methyl-6-(2-[1]naphthyl-vinyl)-2-pyridone
80) 1-methanesulfonyloxy-4-methyl-6-(4-phenyl-buta-1,3-dienyl)-2-pyridone
81) 6-(4-dimethylamino-styryl)-1-methanesulfonyloxy-4-methyl-2-pyridone
82) 1-methanesulfonyloxy-6-(4-methoxy-styryl)-4-methyl-2-pyridone
83) 1-(4-chloro-benzenesulfonyloxy)-6-(4-methoxy-styryl)-4-methyl-2-pyridone
84) 1-(4-chloro-benzenesulfonyloxy)-6-(4-chloro-styryl)4-methyl-2-pyridone
85) 1-ethanesulfonyloxy-6-(4-methoxy-styryl)-4-methyl-2-pyridone
86) 3-bromo-1-methanesulfonyloxy-6-(4-methoxy-styryl)-4-methyl-2-pyridone
87) 1-isopropanesulfonyloxy-6-(4-methoxy-styryl)4-methyl-2-pyridone
88) 1-butanesulfonyloxy-6-(4-methoxy-styryl)-4-methyl-2-pyridone
89) 6-(4-methoxy-styryl)-4-methyl-1-trifluoromethanesulfonyloxy-2-pyridone
90) 6-(4-methoxy-styryl)-(1,1,2,3,3,3-hexafluoropropanesulfonyloxy)-4-methyl-2-pyridone
91) 6-(4-methoxy-styryl)-4-methyl-1-benzenesulfonyloxy-2-pyridone
92) 1-(4-fluoro-benzenesulfonyloxy)-6-(4-methoxy-styryl)-4-methyl-2-pyridone
93) 6-(4-methoxy-styryl)-1-(4-trifluoro-benzenesulfonyloxy)-4-methyl-2-pyridone
94) 1-benzenesulfonyloxy-6-(4-methoxy-styryl)-4-methyl-2-pyridone
95) 6-(4-chloro-styryl)-1-ethanesulfonyloxy-4-methyl-2-pyridone
96) 3-bromo-6-(4-chloro-styryl)-1-methanesulfonyloxy-4-methyl-2-pyridone
97) 6-(4-chloro-styryl)-1-isopropanesulfonyloxy-4-methyl-2-pyridone
98) 1-butanesulfonyloxy-6-(4-chloro-styryl)-4-methyl-2-pyridone
99) 6-(4-chloro-styryl)-4-methyl-1-trifluoromethanesulfonyloxy-2-pyridone
100) 6-(4-chloro-styryl)-1-(1,1,2,3,3,3-hexafluoropropanesulfonyloxy)-4-methyl-2-pyridone
101) 1-benzenesulfonyloxy-6-(4-chloro-styryl)-4-methyl-2-pyridone
102) 6-(4-chloro-styryl)-1-(4-fluorobenzenesulfonyloxy)-4-methyl-2-pyridone
103) 6-(4-chloro-styryl)-4-methyl-1-(4-trifluoromethyl-benzenesulfonyloxy)-2-pyridone
104) 1-benzenesulfonyloxy-6-(4-chloro-styryl)-4-methyl-2-pyridone
105) 1,4-bis-(4-methyl-2-oxo-6-styryl-2H-pyridin-1-yloxysulfonyl)-butane
106) 1,3-bis-[6-(4-methoxy-styryl)-4-methyl-2-oxo-2H-pyridin-1-yloxysulfonyl]-benzene
107) 1,3-bis-[3-bromo-6-(4-chloro-styryl)-4-methyl-2-oxo-2H-pyridin-1-yloxysulfonyl]-2,4,6-trimethylbenzene
108) 1,5-bis-[6-(4-fluoro-styryl)-4-methyl-2-oxo-2H-pyridin-1-yloxysulfonyl]-naphthalene
109) 2-chloro-3,5-bis-[4-methyl-6-(4-methyl-styryl)-2-oxo-2H-pyridin-1-yloxysulfonyl]-thiophene

APPLICATION EXAMPLE 1

This example demonstrates the utility of the compounds according to the invention as acid generators in a positive-working resist layer for planographic printing plates.

An aluminum plate with a mechanically roughened and pretreated surface was coated with a solution of 6.50 p.b.w. of a cresol/formaldehyde novolak (melting range 105° to 120° C. according to DIN 53181),
2.20 p.b.w. of an acetal of piperonal and phenoxyethanol,
0.33 p.b.w. 6-(4-chlorostyryl)-1-methane-sulfonyloxy-4-methyl-2-pyridone and
0.05 p.b.w. of crystal violet base in
30.0 p.b.w. of ethylene glycol monomethyl ether,
52.0 p.b.w. of tetrahydrofuran and
10.0 p.b.w. of butyl acetate in such a way that the layer thickness after drying was about 2 μm. The coated plate was exposed for 20 seconds at a distance of 110 cm under a 5 kW metal halide lamp through an original which, in addition to line and screen motifs, contained a half-tone step wedge with 13 steps each of 0.15 optical density, and, after a waiting time of 15 minutes, developed for 1 minute with a developer of the following composition:

5.5 p.b.w. of sodium metasilicate×9 H₂O,
3.4 p.b.w. of trisodium phosphate×12 H₂O,
0.4 p.b.w. of sodium dihydrogen phosphate (anhydrous) and
90.7 p.b.w. of deionized water.

A positive image close to the original was obtained, in which even the minutest details were exactly reproduced. The printing form obtained was clamped into a sheet-fed offset press and gave more than 65,000 prints of excellent quality.

APPLICATION EXAMPLE 2

This example demonstrates the utility of the compounds according to the invention as acid generators for negative-working photoresists in microelectronics.

A coating solution was prepared from 8.0 p.b.w. of the cresol/formaldehyde novolak mentioned in Application Example 1,
2.0 p.b.w. of hexamethoxymethylmelamine and
0.4 p.b.w. of 6-(4-methoxy-styryl)-4-methyl-1-(4-nitro-benzenesulfonyloxy)-2-pyridone in 56 p.b.w. of propylene glycol monomethyl etheracetate.

The solution was filtered through a filter of 0.2 μm pore diameter and whirler-coated at 3,500 rpm onto a wafer treated with an adhesion promoter (hexamethyldisilazane). After drying for 1 minute at 100° C. on a hotplate, a layer thickness of 1.05 μm was obtained.

The recording material was exposed imagewise under an original, which contained structures as small as 0.2 μm, to the radiation of a xenon-mercury vapor lamp (using a filter with transmission from 360 to 370 nm) at an energy of 80 mJ/cm². The exposed wafer was then heated for 1 further minute at 100° C.

Development was carried out using an aqueous developer which contained 2.38% of tetramethylammonium hydroxide.

After a developing time of 120 seconds, a defect-free negative image of the mask with steep resist flanks was obtained, structures as small as 0.45 μm were resolved in true detail. A scanning electron-microscopic examination of the flanks of the resist profiles proved that these were aligned virtually perpendicular to the substrate surface and showed no undercut.

APPLICATION EXAMPLE 3

This example demonstrates the utility of the compounds according to the invention as UV2-sensitive acid generators for positive-working photoresists in microelectronics.

A coating solution was prepared from 8.0 p.b.w. of a homopolymer of 3-methyl-4-hydroxystyrene having a mean molecular weight of 22,000, 2.0 p.b.w. of the acetal described in Application Example 1 and 0.4 p.b.w. of 4-methyl-6-styryl-1-trichloromethanesulfonyloxy-2-pyridone in 42 p.b.w. of propylene glycol monomethyl etheracetate.

The solution was filtered through a filter of 0.2 μm pore diameter and whirler-coated at 3,200 rpm onto a wafer treated with an adhesion promoter (hexamethyldisilazane). After drying f or 1 minute at 100° C. on a hotplate, a layer thickness of 1.02 μm was obtained.

The recording material was exposed imagewise under an original to the radiation of a xenon-mercury vapor lamp (using a filter with transmission from 240 to 260 nm) at an energy of 80 mJ/cm₂ and, before development, heated on a hotplate for 1 minute to 95° C.

The recording material was developed using an aqueous alkaline developer which contained 2.38% by weight of tetramethylammonium hydroxide.

After a developing time of 90 seconds, this gave a defect-free image of the mask, even structures of <0.4 μm were resolved in true detail. Here again, a scanning electron-microscopic examination of the flanks of the resist profiles showed that these were aligned virtually perpendicular to the substrate surface and, up to this resolution, no covering layer effect was observed.

APPLICATION EXAMPLE 4

This example demonstrates the utility of the compounds according to the invention as light-sensitive photoinitiators for photoresists, polymerizable by a free radical mechanism, for printed circuits.

A coating solution composed of 25.0 p.b.w. of a copolymer of 30 p.b.w. methacrylic acid, 60 p.b.w. of n-hexyl methacrylate and 10 p.b.w. of styrene, 16.5 p.b.w. of a reaction product of 1 mol of 2,2,4-trimethylhexamethylene diisocyanate and 2 mol of hydroxymethyl methacrylate, 1.5 p.b.w. of triethylene glycol dimethacrylate, 0.7 p.b.w. of 1-(4-bromo-benzenesulfonyloxy)-4-methyl-6-(4-trifluoromethyl-styryl)-2-pyridone and 0.1 p.b.w. of 2,4-dinitro-6-chloro-2'-acetylamino-5'-methoxy-4'-(N-β-hydroxyethyl-N-β'-cyanoethylamino)-azobenzene in 60 p.b.w. of methyl ethyl ketone was applied to a polyethylene terephthalate film to a dry layer weight of 25 g/m². This two-layer system was laminated in a commercially available laminator at 120° C. to a support of insulating material which carried a 35 μm thick copper layer. The material was exposed for 60 seconds through an original which, in addition to blind and screen motifs, contained a half-tone step wedge. The light source described in Application Example 1 was used. The exposed material was developed using a 0.8% sodium carbonate solution. This gave a negative of the line and screen motif. Steps 1 to 6 of the half-tone step wedge remained standing as a raised relief, and step 7 was visibly attacked. The bared copper was etched with an iron(III) chloride solution, and the resist layer was not significantly affected.

What is claimed is:

1. A 1-sulfonyloxy-2-pyridone of the formula I

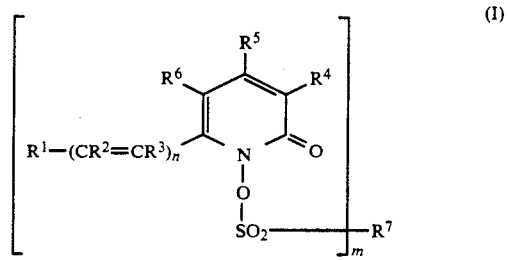

in which

R¹ is an alkyl, cycloalkyl, aryl, aralkenyl, heteroaryl or heteroaralkenyl radical, R² is hydrogen, chlorine, bromine or an alkyl, cycloalkyl, aryl or heteroaryl radical, or R¹ and R² together form a five- to eight-membered ring, R³ is hydrogen or an alkyl radical, R⁴ is hydrogen, halogen, nitro, acylamino, cyano, thiocyanato or an alkyl, alkenyl, alkynyl, aryl, aralkyl, alkylthio, arylthio or cycloalkylthio radical, R⁵ is hydrogen or an alkyl or aryl radical or R⁴ and R⁵ together form a five- to eight-membered ring, R⁶ is hydrogen, halogen, nitro, acylamino, cyano, thiocyanato or an alkyl, alkenyl, alkoxyalkyl, aryl, aralkyl, alkylthio, cycloalkylthio or arylthio radical, R⁷ is an alkyl or cycloalkyl radical, a perfluorinated or highly fluorinated alkyl radical or an aryl, arylalkyl, heteroaryl, alkylene, or arylene radical, m is 1 or 2, and n is 1, 2 or 3.

2. A 1-sulfonyloxy-2-pyridone as claimed in claim 1, wherein R¹ is an alkyl or cycloalkyl radical, or a heterocyclic ring or an aryl radical of the formula II

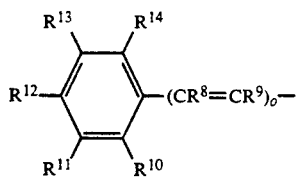 (II)

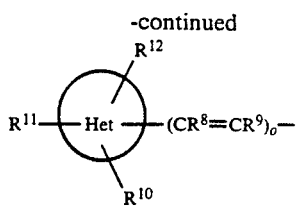 (III)

in which

R$^8$ and R$^9$ are identical or different and are hydrogen or an alkyl or aryl group, R$^{10}$ to R$^{14}$ are identical or different and are hydrogen, an alkyl, alkenyl, alkoxy, alkylthio or alkanesulfonyl radical each having up to 6 carbon atoms, a cycloalkyloxy, cycloalkylthio or cycloalkanesulfonyl radical each having up to 8 carbon atoms, a phenyl, styryl, phenoxy, phenylthio, benzenesulfonyl, phenylalkoxy, phenylalkylthio or phenylalkanesulfonyl radical which may be substituted on the aromatic ring and has up to 3 carbon atoms in the alkyl chain, hydroxy, halogen, trifluoromethyl, nitro, cyano,, alkoxycarbonyl, carbamoyl which may be substituted on the nitrogen by one or two alkyl radicals which may be linked to form a 5- to 7-membered ring, sulfamoyl which may be substituted on the nitrogen by one or two alkyl radicals which may be linked to form a 5- to 7-membered ring, alkanesulfonyloxy, arylsulfonyloxy, acylamino, alkylamino or arylamino, or two mutually adjacent substituents R$^{10}$ to R$^{14}$ form one or two further fused rings, and 0 is 0 or 1.

3. A 1-sulfonyloxy-2-pyridone as claimed in claim 2, wherein R$^1$ is a 5- or 6-membered heterocyclic ring having up to 3 heteroatoms, of the formula III

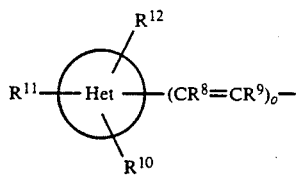 (III)

wherein R$^8$ and R$^{12}$ and o are as defined for formula II.

4. A 1-sulfonyloxy-2-pyridone as claimed in claim 1, wherein,

R$^1$ is a ferrocenyl radical and

R$^2$ is hydrogen, chlorine, bromine, alkyl, cycloalkyl or a radical of the formula

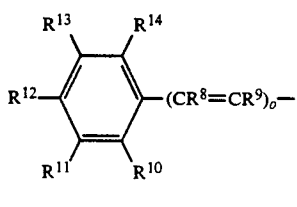 (II)

or wherein

R$^8$ and R$^9$ are identical or different and are hydrogen or an alkyl or aryl group, R$^{10}$ to R$^{14}$ are identical or different and are hydrogen, an alkyl, alkenyl, alkoxy, alkylthio or alkanesulfonyl radical each having up to 6 carbon atoms, a cycloalkyloxy, cycloalkylthio or cycloalkanesulfonyl radical each having up to 8 carbon atoms, a phenyl, styryl, phenoxy, phenylthio, benzenesulfonyl, phenylalkoxy, phenylalkylthio or phenylalkanesulfonyl radical which may be substituted on the aromatic ring and has up to 3 carbon atoms in the alkyl chain,, hydroxy, halogen, trifluoromethyl, nitro, cyano, alkoxycarbonyl, carbamoyl which may be substituted on the nitrogen by one or two alkyl radicals which may be linked to form a 5- to 7-membered ring, sulfamoyl which may be substituted on the nitrogen by one or two alkyl radicals which may be linked to form a 5- to 7-membered ring, alkanesulfonyloxy, arylsulfonyloxy, acylamino, alkylamino or arylamino, or two mutually adjacent substituents R$^{10}$ to R$^{14}$ form one or two further fused rings, or R$^1$ and R$^2$ together form a five- to eight-membered ring, R$^3$ is hydrogen or an alkyl radical, R$^4$ is hydrogen, halogen, nitro, acylamino, cyano, thiocyanato or an alkyl, aryl, alkylthio, arylthio or cycloalkylthio radical, R$^5$ is hydrogen or an alkyl or aryl radical or R$^4$ and R$^5$ together form a five- to eight-membered ring, R$^6$ is hydrogen, halogen, nitro, acylamino, cyano, thiocyanato or an alkyl, aryl, alkylthio, arylthio or cycloalkylthio radical, R$^7$ is an alkyl or cycloalkyl radical, a perfluorinated or highly fluorinated alkyl radical or an aryl, arylalkyl or heteroaryl radical or an alkylene or arylene radical and m is 1 or 2 and n is 1, 2 or 3.

5. A 1-sulfonyloxy-2-pyridone as claimed in claim 1, wherein R$^7$ is an alkyl radical having 1 to 4 carbon atoms, a highly fluorinated or perfluorinated alkyl radical having 1 to 4 carbon atoms or an aryl radical of the formula IV

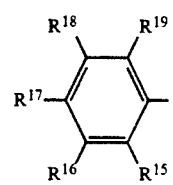 (IV)

in which R$^{15}$ to R$^{19}$ are identical or different and are hydrogen atoms or halogen atoms, alkyl radicals which have up to 6 carbon atoms and are unsubstituted or substituted by halogen atoms, aryl, or aryloxy radicals and in which individual methylene groups can be replaced by oxygen or sulfur atoms, and in which in each case two of these radicals can be linked to form a 5- or 6-membered ring; cycloalkyl radicals having up to 8 carbon atoms, alkenyl radicals having up to 6 carbon atoms or aryl or aryloxy radicals having up to 10 carbon atoms, wherein the total number of the carbon atoms in the radicals $R^{15}$ to $R^{19}$ is not more than 12.

6. A 1-sulfonyloxy-2-pyridone as claimed in claim 1, wherein $R^7$ is a naphthyl or heteroaryl radical having up to 10 carbon atoms, an alkylene radical having up to 6 carbon atoms or an arylene or heteroarylene radical having up to 14 carbon atoms.

7. A 1-sulfonyloxy-2-pyridone as claimed in claim 1, wherein $R^2$, $R^3$, $R^4$ and $R^6$ are each a hydrogen atom, $R^5$ is a methyl group, $R^7$ is a methyl, ethyl, trifluoromethyl, 1,1,2,3,3,3-hexafluoropropyl, phenyl, tolyl, 4-fluorophenyl, 4-chlorophenyl, 4-bromophenyl or 4-nitrophenyl radical, and m and n are each 1.

8. A 1-sulfonyloxy-2-pyridone as claimed in claim 1, which has an absorption maximum in the range between 200 and 550 nm.

9. A 1-sulfonyloxy-2-pyridone as claimed in claim 1, wherein n is 1.

10. A 1-sulfonyloxy-2-pyridone as claimed in claim 1, wherein n is 2.

11. A 1-sulfonyloxy-2-pyridone as claimed in claim 1, wherein m is 1.

12. A 1-sulfonyloxy-2-pyridone as claimed in claim 1, wherein m is 2.

13. A 1-sulfonyloxy-2-pyridone as claimed in claim 2, wherein R1 is of the formula II and o is 0.

14. A 1-sulfonyloxy-2-pyridone as claimed in claim 2, wherein R1 is of the formula II and o is 1.

15. A 1-sulfonyloxy-2-pyridone as claimed in claim 1, wherein each of m and n are 1.

16. A process for preparing a 1-sulfonyloxy-2-pyridone as claimed in claim 1, which comprises the steps of
a) converting a 6-halogenomethyl-2-pyrone with triphenylphosphine into a phosphonium compound or with a trialkylphosphite into a phosphono compound,
b) subjecting this compound to a Wittig reaction or a variant thereof,
c) converting the compound obtained into a 1-hydroxy-2-pyridone by reaction with hydroxylamine, and
d) reacting with a sulfonic acid halide to give a 1-sulfonyloxy-2-pyridone of the formula I.

17. A process as claimed in claim 16, wherein the sulfonic acid halide is a sulfonic acid chloride.

18. A process as claimed in claim 16, wherein the reaction with the sulfonic acid halide is carried out in the presence of an organic phase.

19. A process as claimed in claim 18, wherein the reaction with the sulfonic acid halide is carried out in an organic solvent at temperatures between 0° and 20° C.

* * * * *